(12) United States Patent
Lowe

(10) Patent No.: US 7,713,556 B2
(45) Date of Patent: May 11, 2010

(54) ANTI-TUMOR AND ANTI-INFLAMMATORY EXTRACTS OF PLANT BIOMASS AND THEIR USES

(76) Inventor: Henry Lowe, Eden Gardens, Suite 15, 39 Lady Musgrave Road, Kingston 5 (JM)

( * ) Notice: Subject to any disclaimer, the term of this patent is extended or adjusted under 35 U.S.C. 154(b) by 0 days.

(21) Appl. No.: 12/001,207

(22) Filed: Dec. 10, 2007

(65) Prior Publication Data

US 2008/0145464 A1    Jun. 19, 2008

Related U.S. Application Data

(60) Provisional application No. 60/873,832, filed on Dec. 8, 2006.

(51) Int. Cl.
*A01N 65/00* (2009.01)

(52) U.S. Cl. .................................................. 424/725
(58) Field of Classification Search ................... None
See application file for complete search history.

*Primary Examiner*—Michele Flood
(74) *Attorney, Agent, or Firm*—Ober / Kaler; Royal W. Craig

(57) ABSTRACT

Extracts from an indigenous Jamaican plant that exhibit an anti-tumor activity and/or an anti-inflammatory activity and, more particularly, an extract of Jamaican Ball Moss (*Tillandsia Recurvata*) that has a therapeutic pharmacological activity, in particular an anti-cancerous activity by inducing tumorous cell death by apoptosis, and active compounds isolated thereof are described. Furthermore, methods for the extraction of the extracts are disclosed. Also, a pharmaceutical composition or product for the treatment of cancer which includes an effective amount of the described extract or an active compound thereof, a therapeutic compound and optionally a pharmaceutical acceptable carrier are described.

9 Claims, 14 Drawing Sheets

Anticancer Biological Activity of SFS-CXP Fractions of JEM Biomass
JEM-10-01 – JEM-10-08

| Fraction | Yield (wt. %) | No. of Peaks at 205 nm | Concentration (µg/mL) | No. of Cells | % Killed |
|---|---|---|---|---|---|
| NT | NA | NA | NA | 219,901 | 0.00 |
| JEM-10-01 | 0.42 | 11 | 1,100 | 191,262 | 13.02 |
| JEM-10-02 | 1.51 | 8 | 3,230 | 300 | 99.86 |
| JEM-10-03 | 0.36 | 14 | 790 | 340 | 99.85 |
| JEM-10-04 | 0.18 | 11 | 340 | 548 | 99.75 |
| JEM-10-05 | 0.25 | 11 | 470 | 1,597 | 99.25 |
| JEM-10-06 | 0.19 | 5 | 370 | 62,019 | 70.99 |
| JEM-10-07 | 0.07 | 8 | 340 | 63,351 | 70.37 |
| JEM-10-08 | ND | 5 | 3,000 | 111,538 | 47.83 |

FIG. 3

| Fraction | Yield (wt. %) | No. of Peaks at 330 nm | Dilution | No. of Cells | % Killed |
|---|---|---|---|---|---|
| NT |  |  | 1 | 25,516 | 0.00 |
| JEM-11-08 | < 0.04 | 1 | 1:10 | 2,696 | 89.43 |
| JEM-11-08 |  |  | 1:100 | 5,466 | 78.58 |
| JEM-11-08 |  |  | 1:1000 | 19,439 | 23.82 |
| JEM-11-13 | < 0.04 | 1 | 1:10 | 5,567 | 78.22 |
| JEM-11-13 |  |  | 1:100 | 8,013 | 68.65 |
| JEM-11-13 |  |  | 1:1000 | 17,225 | 32.60 |
| JEM-11-25 | < 0.04 | 0 | 1:10 | 2,008 | 92.13 |
| JEM-11-25 |  |  | 1:100 | 14,061 | 44.89 |
| JEM-11-25 |  |  | 1:1000 | 24,399 | 4.38 |
| JEM-11-26 | < 0.04 | 0 | 1:10 | 1,692 | 93.37 |
| JEM-11-26 |  |  | 1:100 | 28,576 | -11.99* |
| JEM-11-26 |  |  | 1:1000 | 28,502 | -11.70* |
| JEM-11-27 | < 0.04 | 0 | 1:10 | 2,139 | 91.62 |
| JEM-11-27 |  |  | 1:100 | 46,340 | -81.61* |
| JEM-11-27 |  |  | 1:1000 | 34,640 | -35.76* |

*These negative values probably resulted from poor negative controls.

FIG. 4

| Fraction JEM-11- | Starting Volume (mL) | Final Weight (mg) | Projected Weight (mg) | Estimated Yield* (%) | Concentration (mg/mL) | Fraction JEM-12- |
|---|---|---|---|---|---|---|
| 08 | 33.5 | 1.4 | 2.13 | 0.016 | 1.4 | 08 |
| 13 | 33.5 | 1.0 | 1.49 | 0.012 | 1.0 | 13 |
| 25 | 19.0 | 0.7 | 1.84 | 0.014 | 0.7 | 25 |
| 26 | 19.5 | 1.2 | 3.08 | 0.024 | 1.2 | 26 |
| 27 | 19.5 | 1.5 | 3.85 | 0.030 | 1.5 | 27 |

* Yield based on 28.059 grams of JEM Biomass, and assuming proportional quantities of these fractions in JEM-10-3, JEM-10-4 and JEM-10-5

$y = 0.3181x^4 + 5.8462x^3 + 2.5759x^2 - 2.2885x + 53.211$
$R^2 = 1$

Log Concentration versus Percentage Kill Efficiency for JEM-12-25

Anticancer Activity of Concentrated Bioactive Anticancer Fractions/Compounds (JEM-12-08, JEM-12-13 and JEM-12-25)

| Fraction | Dilution | Concentration (µg/mL) | No. of Cells | % Killed |
|---|---|---|---|---|
| Cells+Medium | 1 | 0 | 76,995 | 0.00 |
| JEM-12-08 | 1:10 | 140 | 1,836 | 97.61 |
| JEM-12-08 | 1:100 | 14 | 29,457 | 61.72 |
| JEM-12-08 | 1:1,000 | 1.4 | 35,034 | 54.48 |
| JEM-12-08 | 1:10,000 | 0.14 | 47,985 | 37.73 |
| JEM-12-08 | 1:100,000 | 0.014 | 61,658 | 19.91 |
| Cells+Medium | 1 | 0 | 76,995 | 0.00 |
| JEM-12-13 | 1:10 | 100 | 682 | 99.11 |
| JEM-12-13 | 1:100 | 10 | 18,264 | 76.26 |
| JEM-12-13 | 1:1,000 | 1 | 59,211 | 23.08 |
| JEM-12-13 | 1:10,000 | 0.1 | 59,945 | 22.17 |
| JEM-12-13 | 1:100,000 | 0.01 | 64,131 | 16.70 |
| Cells+Medium | 1 | 0 | 76,995 | 0.00 |
| JEM-12-25 | 1:10 | 70 | 1,413 | 98.17 |
| JEM-12-25 | 1:100 | 7 | 33,240 | 56.81 |
| JEM-12-25 | 1:1,000 | 0.7 | 35,703 | 53.61 |
| JEM-12-25 | 1:10,000 | 0.07 | 37,861 | 50.85 |
| JEM-12-25 | 1:100,000 | 0.007 | 62,780 | 18.46 |

FIG. 8

50% Effective Concentrations ($EC_{50}$) of (JEM-12-08, JEM-12-13 and JEM-12-25)

| Fraction | $EC_{50}$ (µg/mL) (Graphical Interpolation) | $EC_{50}$ (µg/mL) (Best Fit Equation) |
|---|---|---|
| JEM-12-08 | 0.622 | 0.540 |
| JEM-12-13 | 3.793 | 3.237 |
| JEM-12-25 | 0.070 | 0.000192 |

FIG. 9

ANTI-TUMOR AND ANTI-INFLAMMATORY EXTRACTS OF PLANT BIOMASS AND THEIR USES

CROSS-REFERENCE TO RELATED APPLICATION(S)

The present application derives priority from U.S. provisional Application No. 60/873,832 filed 8 Dec. 2006.

BACKGROUND OF THE INVENTION

1. Field of the Invention

The present invention relates to a therapeutic extract derived from plant biomass for use in regressing cancerous tumors and/or for anti-inflammatory effect and, specifically, to a pharmacologically active compound extracted from the indigenous Jamaican plant Ball Moss (*Tillandsia Recurvata*) that has beneficial activity principally in destroying cancer cells.

2. Description of the Background

There is great growth in the overlapping fields of biology, technology, and medicine, including remarkable advances in cellular biology that have given a new understanding of the molecular basis for some diseases. Nevertheless, the incidence of some forms of cancer continues to rise. This is particularly true of breast cancer, a leading cause of death in women. Considerable effort has focused on the early detection of cellular transformation and tumor formation in breast tissue.

The increased focus on cellular biology has led to a profusion of drugs to treat cancer patients are drugs, which more or less directly target the growth mechanism. These drugs include alkylating agents, intercalating agents, antimetabolites, etc., most of which target DNA or enzymes regulating the DNA duplication and elongation process. However, rapidly growing tumors do not always exhibit high levels of cell proliferation, but may also exhibit low levels of cell death compared to the normal cell population from which these tumor cells issue. For these types of rapidly growing tumors, the mentioned drugs are not effective. In addition, the great majority of the drugs currently available for treatment of cancer are toxic and involve detrimental side-effects on healthy cells, tissues and organs.

The high-technology approach has obfuscated many promising therapeutic drugs derived from natural origins. A successful anticancer drug should kill or incapacitate cancer cells without causing excessive damage to normal cells. This ideal situation is achievable by inducing apoptosis in cancer cells without undue side effects, and organic drugs are well-suited. Apoptosis is a programmed cell death initiated by the nucleus. Apoptosis is a mechanism of cell death that incurs little or no inflammatory response. Currently, radiation is effective in producing cell death by apoptosis but is dependent on dose rate as well as ionization density, and this subjects other non-tumor cells to radiation risks.

Natural products are the most consistently successful source of drug leads. They are likely to continue to be sources of new commercially viable drug leads. Plants supply most of the active ingredients of traditional medicinal products. Advances in the treatment of cancer will require the continued development of novel and improved chemotherapeutic agents.

Therefore, there remains a need in the art for finding organic anti-cancer drugs that overcome at least some of the above-mentioned drawbacks.

SUMMARY OF THE INVENTION

It is, therefore, the primary object of the present invention to provide a therapeutic drug from natural extracts that kills cancerous tumor cells by apoptosis.

It is another object to provide an anti-cancerous therapeutic drug as above, derived from the indigenous Jamaican plant: Ball Moss (*Tillandsia Recurvata*).

It is another object to provide an anti-cancerous therapeutic drug derived from an indigenous Jamaican plant that has an added potential anti-inflammatory effect.

The present invention is a therapeutic drug derived alternatively from an extract of indigenous Jamaican plant biomass for use in regressing cancerous tumors and/or for anti-inflammatory effect. The extract is derived from Jamaican Ball Moss (*Tillandsia Recurvata*). The extract is used as an anti-cancer drug with possibly other therapeutic uses (i.e. anti-inflammatory), and a high-level of efficacy has been shown by positive test results.

BRIEF DESCRIPTION OF THE DRAWINGS

Other objects, features, and advantages of the present invention will become more apparent from the following detailed description of the preferred embodiment and certain modifications thereof when taken together with the accompanying drawings in which:

FIG. 3 shows the results of a JEM assay together with fractional yields and integrateable chromatographic peaks of the anticancer bioactivities of JEM-10 fractions.

FIG. 4 shows in vitro results from the major bioactive fractions in JEM-11 against an aggressive B16 melanoma tumor cell line.

FIG. 8 shows in vitro results from the major bioactive fractions in JEM-12 against an aggressive B16 melanoma tumor cell line.

FIG. 9 summarizes the 50% effective concentrations (EC50) of JEM-12-08, JEM-12-13 and JEM 12-25.

DETAILED DESCRIPTION OF THE PREFERRED EMBODIMENTS

The present invention is a therapeutic extract derived from plant biomass, and specifically an indigenous Jamaican plant, for use in regressing cancerous tumors and/or for anti-inflammatory effect. The therapeutic drug extract is derived from Jamaican Ball Moss (*Tillandsia Recurvata*).

*Tillandsia recurvata* is more commonly known as Ball Moss, Bunch Moss, Tree Hair, French Hair, and Spanish Beard, and comes from the plant species of the Pineapple. It is an air plant indigenous to Jamaica, and it is commonly thought to bring good luck to carry a bit of the Ball moss around on one's person. It was not heretofore known to have any pharmacological value. For purposes of description Jamaican Ball Moss is herein abbreviated as JEM.

In accordance with the present invention glycoside extracts from JEM plant biomass are isolated, their structure determined and their biological activity as anti-cancer drugs with possibly other therapeutic uses (i.e. anti-inflammatory) are investigated. Initial efficacy results across a wide range of cancer cell lines are competitive with a number of clinically proven anticancer agents including Paclitaxel (Taxol®), isolated from the bark of the Pacific Yew tree, and cytotoxicity is much lower. The term "glycoside" as used herein means a derivative of a sugar in which the hydroxyl group attached to carbon 1 of the sugar is substituted by an alcoholic, or other, aglycone group. The curative extracts described herein are glycosides containing one or two sialic acids, and a plurality of amines present within the structure and having a molecular mass of approximately 1601.

Figure 1:
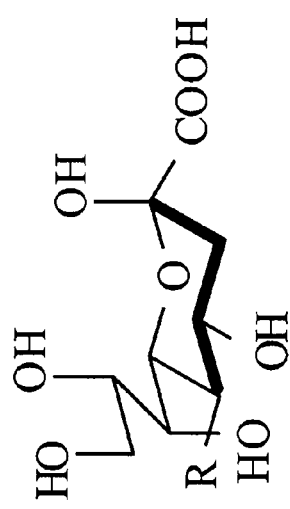
FIG. 1 is a molecular diagram of the structure of sialic acid.

FIG. 1 is a molecular diagram of the structure of sialic acid, which is a member of a structurally unique family of 8 and 9-carbon monosaccharides and characteristically containing ananomeric carboxylate, a deoxygenated methylene C-3 ringcarbon, and an oligohydroxylated side chain at C-6. Sialic acid is differentially functionalized at C-5. The present therapeutic glycoside extract contains one-to-two sialic acids, and a number of amines n present within the structure, where n is an integer less than or equal to two. The test molecule described below was found to carry two positive charges, whereupon it was concluded that there must two amines present within the molecular structure. The curative JEM extract has a resulting molecular mass of 1601.1 Da (in the negative ionization mode), molecular weight of ~800, and a UV spectra maxima at 193.7 nm.

Figure 2:
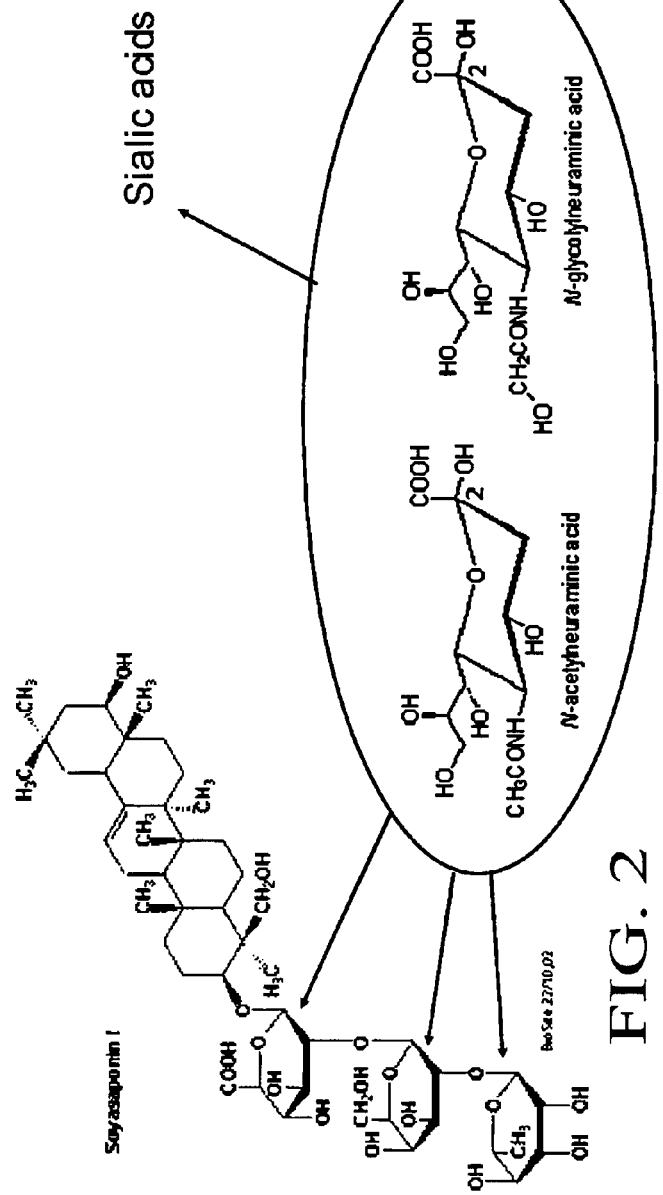
FIG. 2 is a molecular diagram of an exemplary JEM extract according to the present invention.

Thus, as seen in FIG. 2, an exemplary JEM extract is an aliphatic molecule with double and triple carbon bonds (CH2 and CH3), specifically comprising 1-3 sugar rings, several aliphatic rings, and optionally a hydrocarbon chain(s). There are at least 6 methyl (CH3) groups, and on the order of 10 CH2 and CH groups. There is also evidence of at least one likely amide to aliphatic proton.

An exemplary method for the isolation of the above-described anticancer bioactive is described below using bioassay-guided fractionation and chromatographic purification, as are the potent in vitro and in vivo anticancer test results on several different refractory cancer cell lines.

1. Extraction

For extraction, JEM plant samples are collected, and air-dried. Preliminary polarity-guided fractionation experiments were conducted on the dried JEM biomass utilizing a bioassay-guided fractionation approach as set forth in U.S. Pat. No. 5,854,064 to Castor et al. issued Dec. 29, 1998, which disclosure is herein incorporated by reference in its entirety. In this process supercritical and near critical fluids are used to fractionate the JEM biomass material in two steps. In the first step, the JEM biomass is exposed to elevated pressure supercritical or near critical fluid to bring about disruption of the biomass. In the second step, the disrupted biomass is subjected to a multiplicity of supercritical or near critical fluid extraction steps, with different solvation conditions used for each fraction. These solvation conditions were varied from 100% carbon dioxide ($CO_2$) and ending with 100% methanol ($CH_3OH$) to effect fractionation of the biomass. Twenty-eight (28) fractions were produced, two of which were methanolic fractions. High-performance liquid chromatography-photodiode array detector (HPLC-PDA) analysis of all fractions was conducted measuring the entire UV spectra and documenting the UV response at 2 wavelengths, 205 nm and 280 nm. Then all of these were then tested in vitro against the potent melanoma B-16 cell lines. The efficacy of the fractions against the B-16 cell lines was measured using very sensitive Trypan Blue Exclusion in vitro assays, which are conventional dye exclusion test used to determine the number of viable cells present in a cell suspension. They are based on the principle that live cells possess intact cell membranes that exclude certain dyes, such as trypan blue. The Trypan Blue Exclusion in vitro assays identified two fractions that killed approximately 100% of the B-16 cells at an equivalent concentration of 1.0 mg/mL, and appeared to be nontoxic from preliminary in vivo (animal) studies. One of the bioactives was a methanolic fraction and one was not.

Additional fractionations were then conducted to narrow the polarity region in which these active component or components are located. These additional experiments were conducted with both the original JEM biomass and the methanolic extract described above to determine the preferred matrix of isolating the anticancer bioactive constituents. The original sample of biomass was extracted with supercritical fluids as above but on a schedule designed to identify the most bioactive fraction and to exhaustively extract this fraction from the biomass. Also, the viscous, solvent-free methanolic extract was first extended on a solid support matrix and then subjected to supercritical fluid fractionation under the same conditions as above, and after preparative silica chromatography, and preparative reverse phase chromatography on a CG71 polymeric matrix. The supercritical fluid fractionation of the biomass yielded 6 fractions and the supercritical fluid fractionation of the methanolic extract also yielded 6 fractions. The silica chromatography of the methanolic extract yielded 9 fractions and the CG71 chromatography of the methanolic extract yielded 11 fractions. Thus, 32 fractions were obtained in addition to an organic extract of the original solvent-free methanolic extract and an extract of components of low methanol solubility.

Again, all of these fractions were then tested in vitro against the potent melanoma B-16 cell lines.

The most bioactive fraction in the initial study was then compared to the most bioactive fraction in this series of experiments by identify eluting peaks with a common UV spectrum. The UV spectra of the first eluted at 18.721 minutes and the second eluted at 18.230 minutes. These seem remarkably similar, suggesting that the bioactive compounds in the two fractions are most likely the same compound. The above-described SuperFluids™ fractionation approach was then used to obtain a purified methanol extract from dried and ground JEM biomass; and the most bioactive fractions were identified using reversed phase or silica chromatography.

To establish the purification step and parameters for its scale-up, a semi-preparative chromatographic purification was conducted on an analytical scale C18 HPLC column in an experiment labeled "JEM-08." This experiment was designed based on the elution profiles of the preliminary studies under different gradients on an analytical scale C18 HPLC column. The data from this experiment indicate that JEM-08-11 was the most significant bioactive fraction of the preparatory scale C18 chromatographic purification of SFS-CXF 0305. The data also indicated that the original sample material (SM) retained its biological activity even after it had been stored for 3 to 4 months at 5° C.

The next steps of the isolation process include scaling up both the fractionation and the chromatographic purification steps. Based on the previous results, we elected to scale up the SuperFluids™ CXF fractionation run to produce a larger amount of material. The fractionation run was scaled up in a bench-scale SuperFluids™ CXP unit, which consists of a 127-mL extraction column (rated for 10,000 psig) and a 50-mL chromatographic column (rated for 10,000 psig). The equipment was thoroughly cleaned and the cleaning solvent tested for chemical residues. After cleaning, and determination that operating parameters and design conditions were acceptable, an SFS-CXP run was conducted on 28.059 grams of dried, ground JEM biomass. Seven (7) fractions were obtained (JEM-10-2 . . . 8). Fractional yields were then computed taking a small aliquot of known volume and drying under moderate heat in a vacuum and with centrifugal force utilizing a Savant Speed Vac. The overall yield of 2.98 wt % in JEM-10 was around the same as the preliminary fractions (2.38% and 2.74%). Gradient RP-HPLC-PDA analyses were conducted on all JEM-10 fractions measuring the entire UV spectra of eluting peaks and documenting the UV response at 1 wavelengths, 205 nm and 280 nm. HPLC assays were performed on a Phenomenex Luna column with an acidic acetonitrile: water mobile phase at 30° C. and a flowrate of 1.0 mL/n JEM-10-08, the waxy precipitate isolated, had a single peak at 61.518 minutes with a unique I spectrum that was different from those of previous bioactive fractions. The elution time confirms the nonpolar characteristic of JEM-10-8 that was likely isolated in the first fraction of JEM-10 suggesting that this fraction was not exhaustive and needs to be extended in future large-scale SFS-CXP runs.

The anticancer bioactivities of JEM-10 fractions including JEM-10-08 were measured utilizing the extremely sensil 3H thymidine incorporation in vitro assay against an aggressive B16 melanoma tumor cell line. The results of this assay together with fractional yields and integrateable chromatographic PE at 205 nm are summarized in FIG. 3. The data in FIG. 3 indicates that the anticancer bioactivity is concentrated in fraction JEM-10-04.

The analytical chromatographic purification scaled up for preparatory-scale purification of JEM-10-03 on a preparatory-scale C18 HPLC column in experiment JEM-11. The initial HPLC scan on JEM-03-05 used a gradient from 10% ACN to 100% ACN in 60 minutes at 1.5 mL/min. The first significant peak eluted at 16 minutes with an effective time of 14 minutes to compensate for the void volume of the column. Since the ACN concentration was increasing at 1.5%/minute, the time of 14 minutes corresponds to an increase in % ACN of 21%. Since the initial ACN was 10%, the ACN concentration at the time of the elution of the first peak was 31%. For low percentages of methanol and acetonitrile, the acetonitrile is approximately twice as effective in moving components, as is methanol. For example, 31% ACN will produce approximately the same chromatographic motion as ca 55% methanol.

This suggests that if the sample could be dissolved in a solvent weaker than 55% methanol, the sample could be loaded onto the preparative column with good retention. This approach was carried out successfully through a 35× scale-up of chromatographic conditions and operations. The column used was a 25-cm 10 micron 21.2 mm ID Synergi™ column (Phenomenex, Calif.). Chromatography was performed using a Waters LC4000 Prep pump. Fifty (50) fractions were obtained from JEM-11. Gradient RP-HPLC-PDA analyses were conducted all fifty (50) JEM-11 fractions, measuring the entire UV spectra of eluting peaks and documenting the UV response at two wavelengths, 280 nm and 330 nm; the latter because of the intensity of the UV spectra of major peaks in the loading sample. HPLC assays were performed on a Phenomenex Luna C18 column with an acidic acetonitrile:water mobile phase at 30° C. and a flowrate of 1.0 mL/min. Again, the anticancer bioactivities of JEM-11 were measured utilizing the extremely sensitive 3H thymidine incorporation in vitro assay against an aggressive B16 melanoma tumor cell line. Results from the major bioactive fractions in JEM-11 are summarized in FIG. 4.

The data in FIG. 4 indicates that JEM-11-26 is the most bioactive of the five bioactive fractions, bracketed by only slightly less bioactive fractions JEM-11-25 and JEM-11-27. The remaining volumes from fractions JEM-11-08, JEM-11-13, JEM-11-25, JEM-11-26 and JEM-11-27 were dried down to solids in pre-weighed 15-mL centrifuge tubes in a Speed-Vac™ overnight under vacuum at low to moderate temperature conditions. The tubes were then weighed to get the tare weight of the fractions, which were the reconstituted in 1.0 mL methanol, and identified as JEM-12-08, JEM-12-13 and JEM-12-25. The samples were stored at 4° C. until used. The yields and concentrations are listed in FIG. 5.

Assuming that the bioactivities in JEM-12-25, JEM-12-26 and JEM-12-27 are based on a single compound with a weak or no chromophore, its yield from the JEM biomass is estimated to be 0.068%. This yield is similar to but a bit higher than yields (0.02 to 0.05%) typically seen with Paclitaxel, which is isolated from the bark of the *Taxus brevifolia* tree and from the needles or leaves of the *Taxus media "hicksii"* ornamental shrub.

Figure 6:
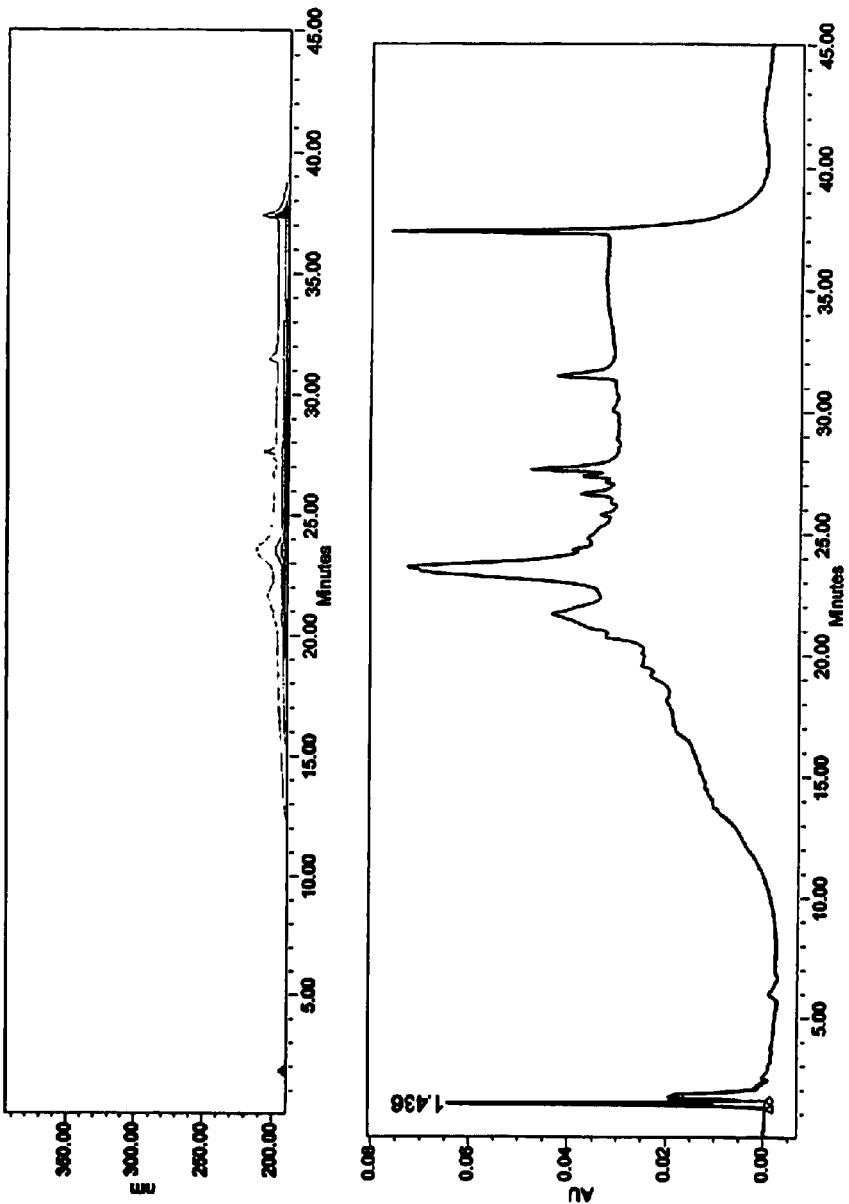
FIGS. 6 and 7 are chromatograms of JEM-12-25 from gradient RP-HPLC-ELSD and PDA analyses, respectively, conducted on the JEM-12 fractions.
Figure 7:
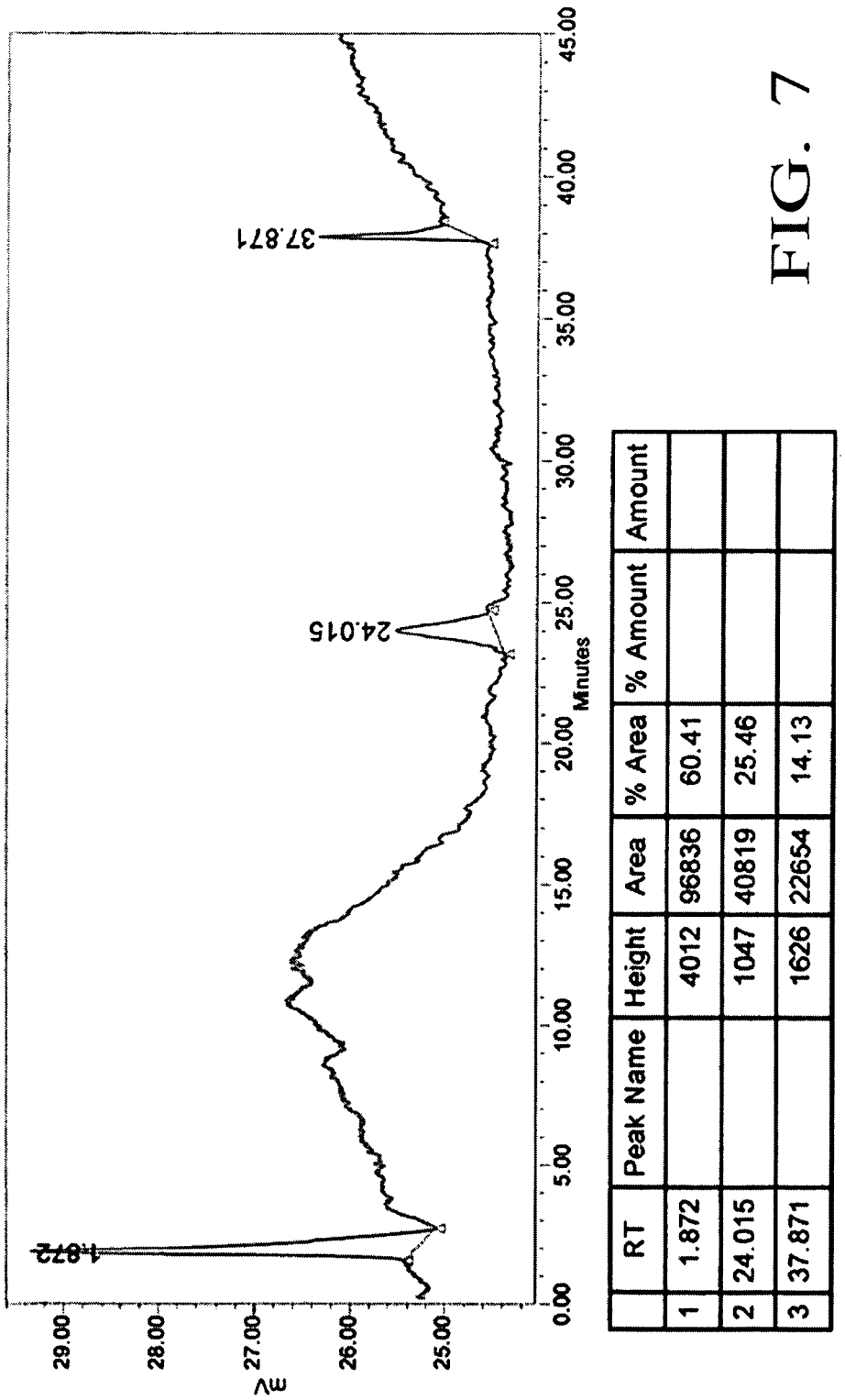

FIGS. 6 and 7 are chromatograms of JEM-12-25 from gradient RP-HPLC-ELSD and PDA analyses, respectively, conducted on the JEM-12 fractions in order to detect the presence of mass that may or may not have a UV spectra while measuring the entire UV spectra of eluting peaks that do have a UV spectra and documenting the UV response at a wavelength of 205 nm. HPLC assays were performed on a Phenomenex Luna C18 column with an acidic acetonitrile:water mobile phase at 30° C. and a flowrate of 1.0 mL/min. The chromatograms indicate the presence of a single compound elution at 24.015 minutes after elution of chromatographic peaks generated from the methanol vehicle.

The anticancer bioactivities of JEM-12-08, JEM12-13 and JEM-12-25 fractions were measured utilizing the extremely sensitive 3H thymidine incorporation in vitro assay against an aggressive B16 melanoma tumor cell line. The results are summarized in FIG. 8, and clearly JEM-12-08, JEM-12-13 exhibited high kill rates.

FIG. 9 summarizes the 50% effective concentrations (EC50) of JEM-12-08, JEM-12-13 and JEM 12-25, and this illustrates that JEM-12-25 is by far the most bioactive fraction. The EC50 is a statistically derived concentration of the compound in an environmental medium expected to produce a certain effect in 50% of the test organisms (Mice) under defined conditions. (Duffus, 1993).

In summary, the EC50 of JEM-12-25 is approximately 0.070 Ipg/mL or 70 nanograms/mL per the listing in FIG. 9.

Figures 5, 10:
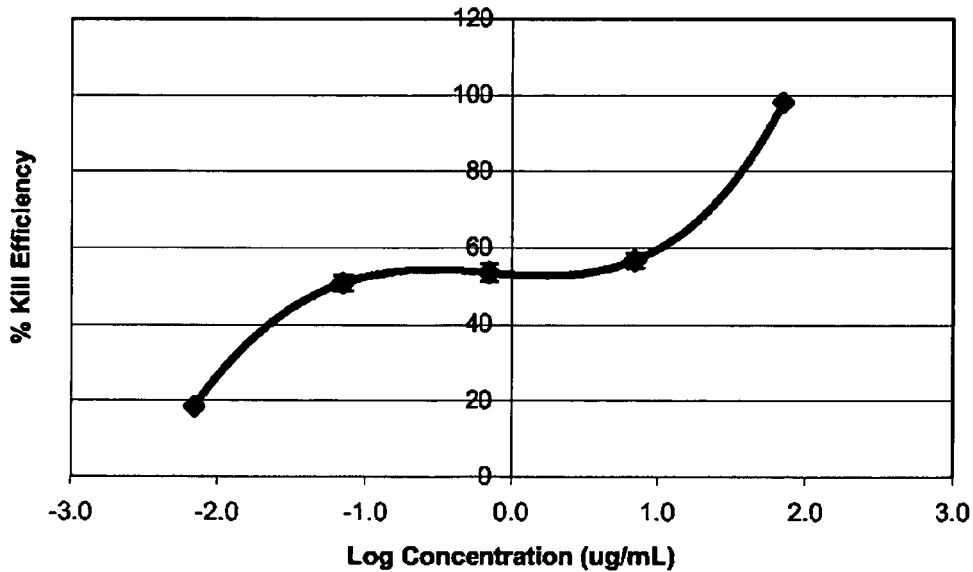
FIG. 5 shows the yields and concentrations of JEM-12-08, JEM-12-13 and JEM-12-25.
FIG. 10 is a graph plotted as log-to-the-base-10 of concentration versus percentage kill efficiency which illustrates the anticancer bioactivity data for JEM-12-25.

FIG. 10 is a graph plotted as log-to-the-base-10 of concentration versus percentage kill efficiency which illustrates the anticancer bioactivity data for JEM-12-25. Based on the equation in FIG. 10 (top) the EC50 computes out to be 0.000192 Ipg/mL or 0.192 nanograms/mL. This confirms that JEM-12-25 is the most bioactive fraction, with results competitive with a number of clinically proven anticancer agents including Paclitaxel (Taxol®), isolated from the bark of the Pacific Yew tree.

2. Efficacy Test Results

A. In-vitro Results

Figure 11:
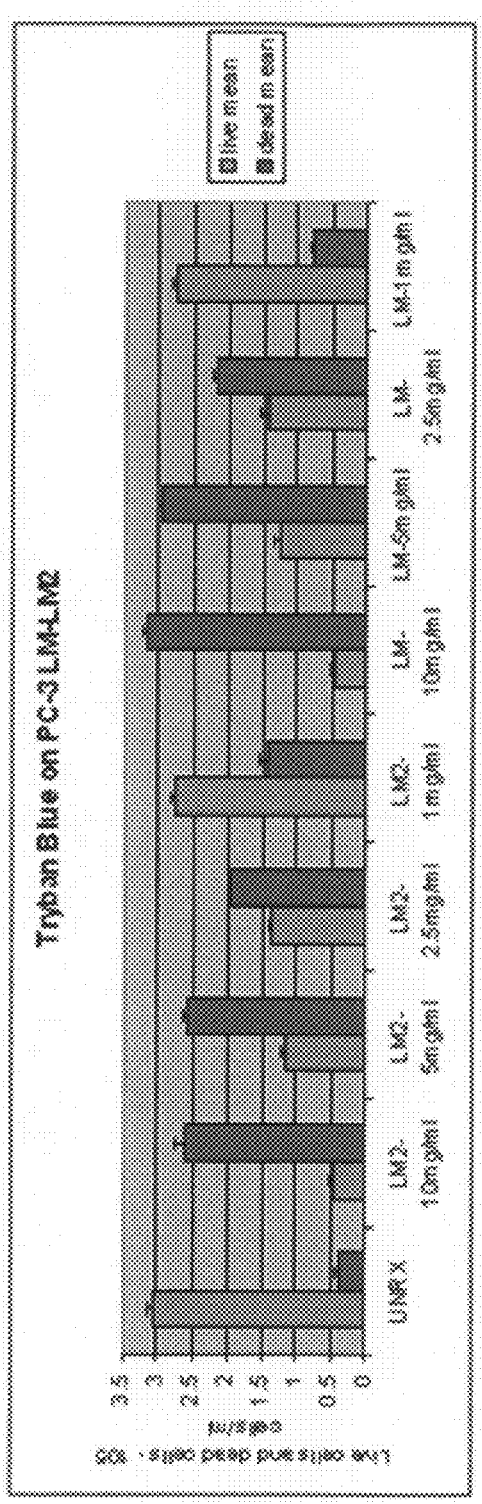
FIG. 11 is a graphical illustration of the in vitro results on Prostate Cancer (PC-3).
Figure 12:
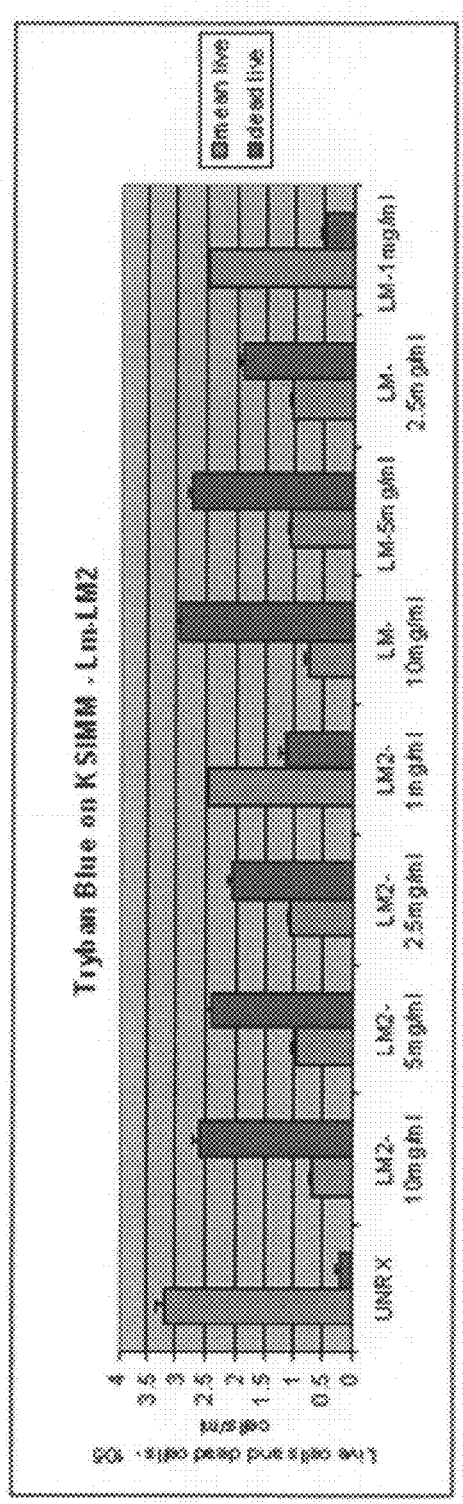
FIG. 12 is a graphical illustration of the in vitro results on Kaposi Sarcoma (K SIMM).
Figure 13:
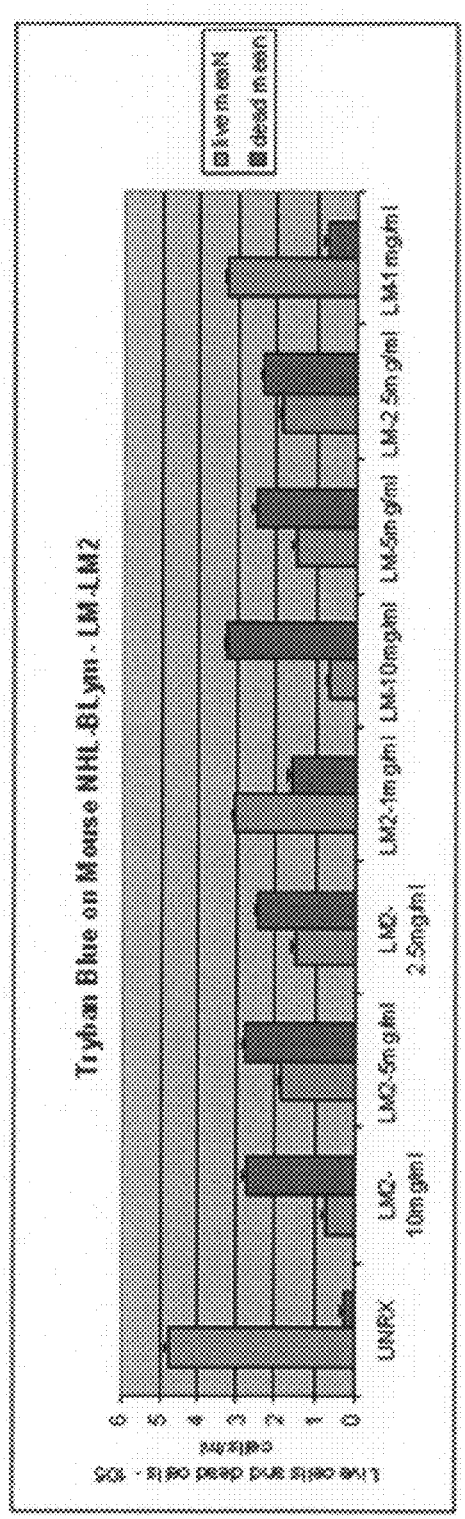
FIG. 13 is a graphical illustration of the in vitro results on B-Cell Lymphoma (BLym).
Figure 14:
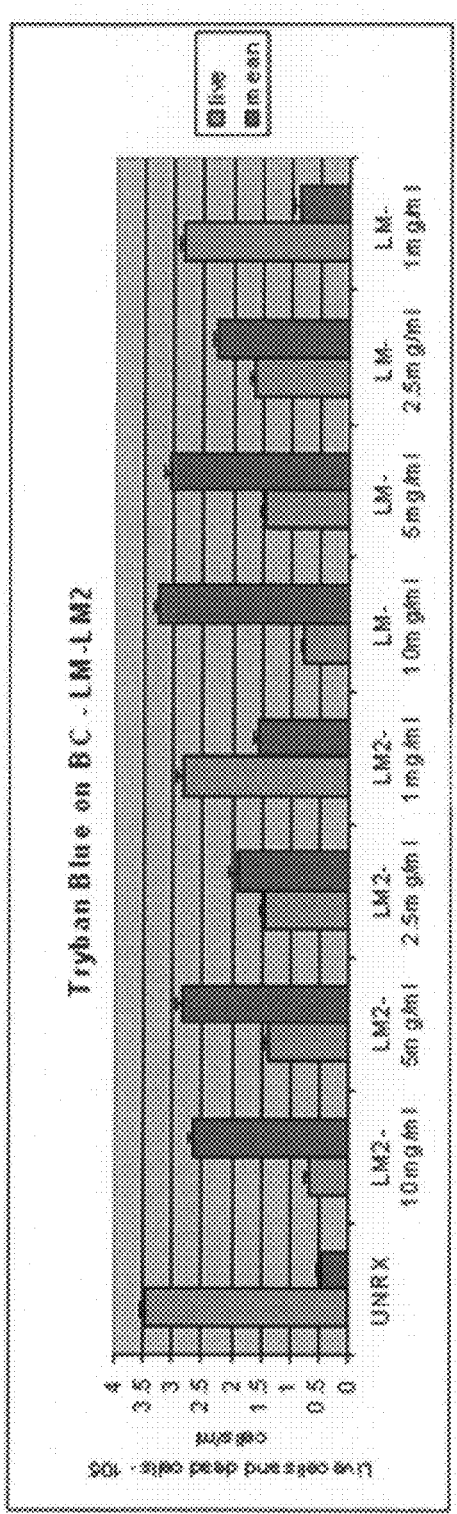
FIG. 14 is a graphical illustration of the in vitro results on Breast Cancer (BC).
Figure 15:
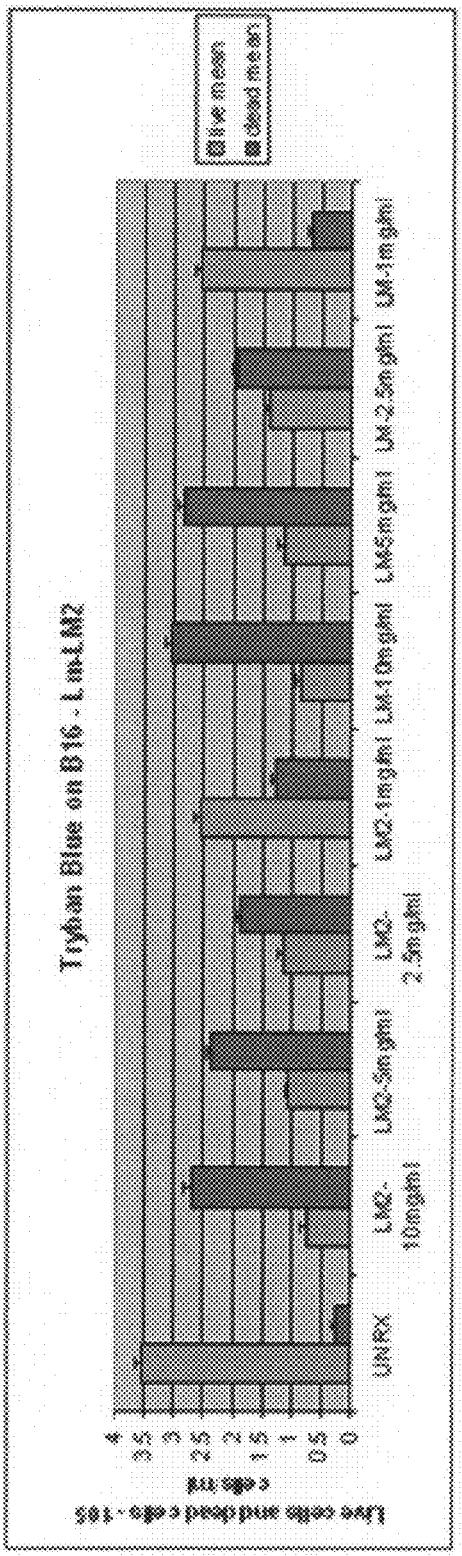
FIG. 15 is a graphical illustration of the in vitro results on B-16 Melanoma (B16).
Figure 16:
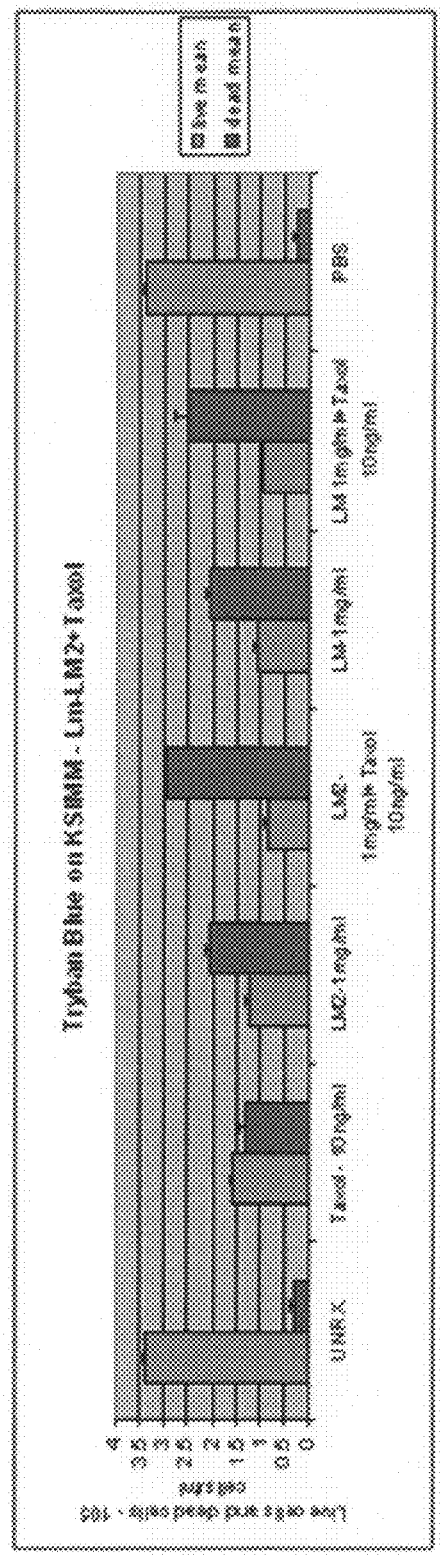
FIGS. 16-20 show the comparative Taxol™ results corresponding to FIGS. 11-15.
Figure 17:
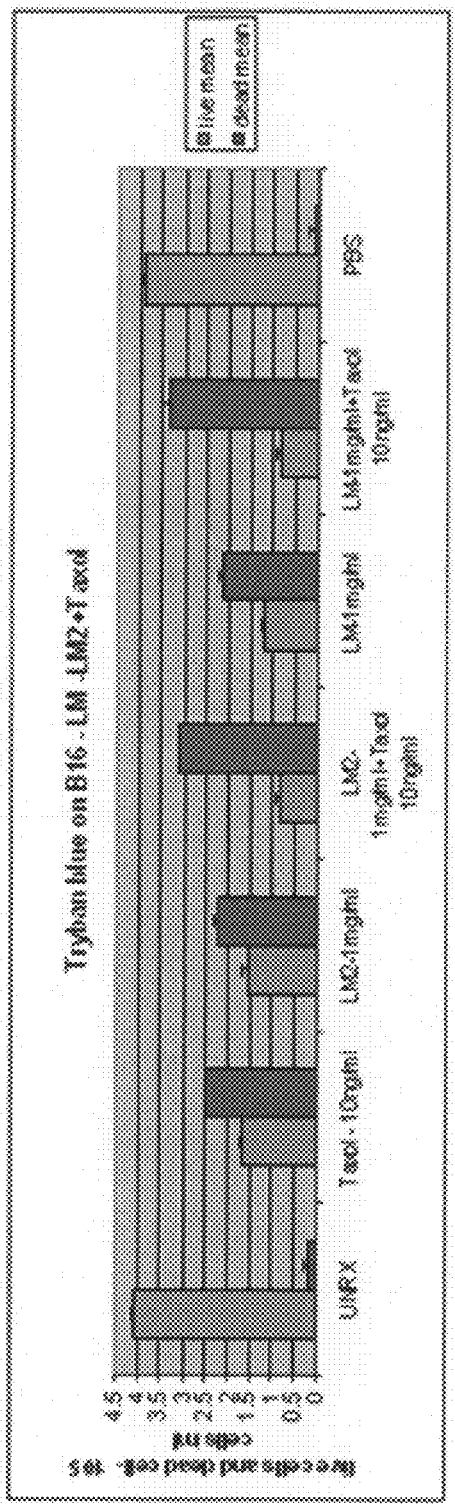
Figure 18:
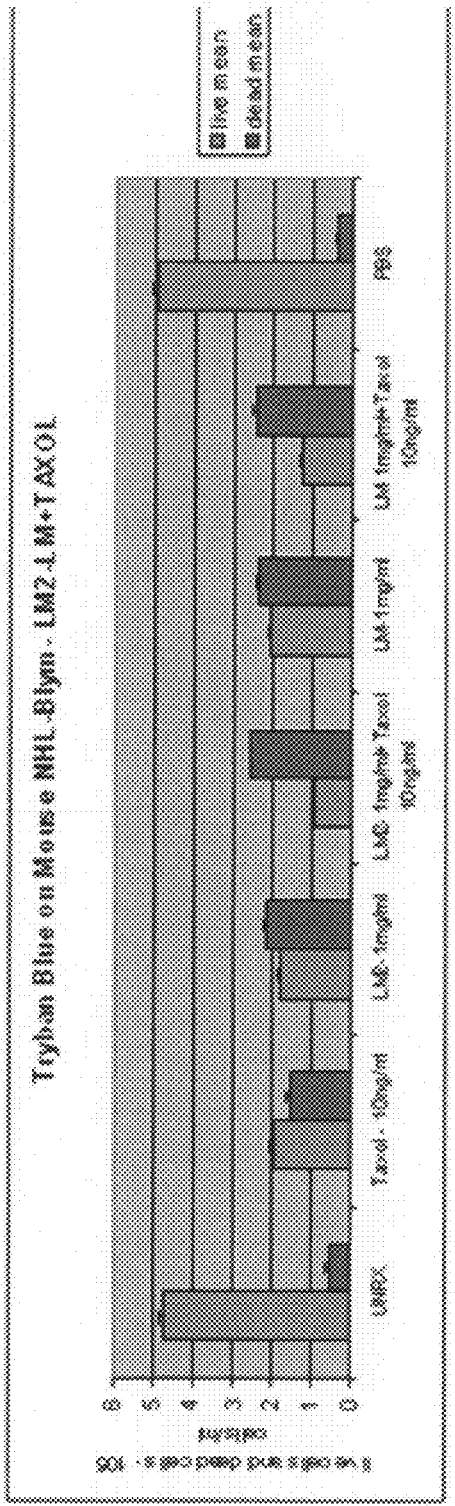
Figure 19:
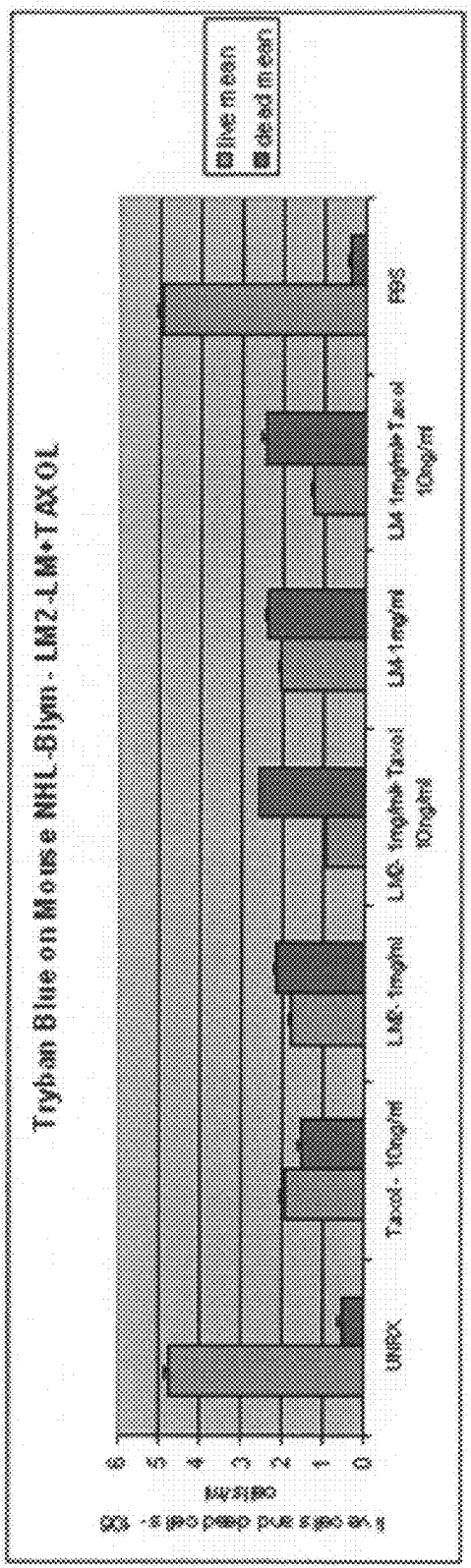
Figure 20:
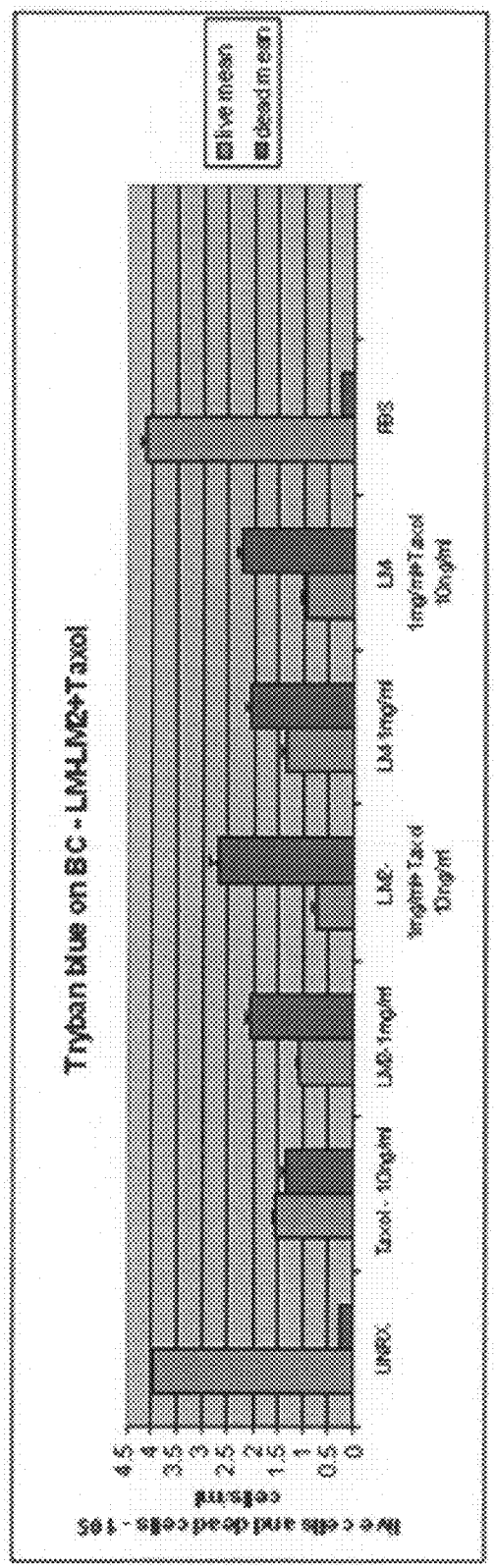

The effects of the JEM plant-derived extracts were tested against four additional tumor cell lines including Breast Cancer, Prostate Cancer, Kaposi Sarcoma, and a B-Cell Lymphoma line. It proved highly positive against these cancers both in vitro and in vivo. Using the same above-described methods and materials, FIG. 11 illustrates the in vitro results on Prostate Cancer (PC-3), while FIG. 12 shows the results for Kaposi Sarcoma (K SIMM). FIG. 13 shows B-Cell Lymphoma (BLym), FIG. 14 shows Breast Cancer (BC), and FIG. 15 illustrates B-16 Melanoma (B16). The comparative Taxol™ results are show in FIGS. 16-20. The graphs illustrate that the *Tillandsia Recurvata* extracts exhibit statistically significant effects comparable to the Taxol™ for killing the tumor cells.

B. In-vivo Results

In vivo tests were also performed on mice to demonstrate the cytotoxicity and the apoptotic effects of *Tillandsia Recurvata* on these tumors. The tumor cell lines were injected subcutaneously of one million cells per tumor cell lines. The different tumors grew at different rates, ranging from three to five weeks to grow to the volume for the different treatments, usually at 1-2 mm. At this stage the tumors were treated daily at dose of 5-10 mg/per mm subcutaneously for seven days. On day eight the tumors were removed, collected and fixed for preparation to be stained with H&E and a special stain (apoptotic) which demonstrates cell depth. All control mice were treated with normal saline and prepared the same as for the treated tumors.

To evaluate the anti-cancer properties of the extract nude mouse tumor zenograft was used, which is a widely accepted model for evaluating anti-tumor efficacy of a test agent and associated toxicity. Proliferation, apoptosis and angiogenesis are the most reliable and common biomarkers to assess efficacy of a compound on tumor growth and progression. In accord with these standards it was observed, after subcutaneous injections of the extracts in the tumor zenograft growth in the nude mice, significant inhibition of tumor growth without any apparent toxicity. The B-16 melanoma tumor was grown in the C57 Black/6, which is an immunocompetent mouse strain. The tumor volume data (not shown) reflected that there was a significant increase in tumor volume between control and all of the treatment groups. In addition, combination therapy of the use of the extracts with Taxol™ at a much lower dose showed an additive effect, suggesting synergy on the tumor growth inhibition. Histological examination of H&E stained lesions of the different tumors treated with the extracts showed a central regression of the tumor cell characterized by cells with pynotic nuclei inflammatory cell infiltration (macrophages, polymorphnuclear cells), and absence of blood vessels especially in the Kaposi Sarcoma tumors. No signs of lesion regression were observed in the control lesions.

An apoptotic cell death assay was also performed utilizing a commercial available in situ apoptosis detection kit (Apop Tag, Oncor™). This procedure works by immunohistochemistry in which the slides are evaluated based on the cells taking up the stain (brown), indicating the cells have undergone apoptosis. In all five histogenic tumors it was demonstrated that apoptosis occurred at a rate of 80% to 90% of the tumor cell death on histology. There was extensive necrosis and apoptosis. Clearly, the *Tillandsia Recurvata* extract has demonstrated efficacy on a par with Taxol™ and other cancer drugs for killing tumor cells. In addition, it was found that administering the JEM extract to a chronic inflammatory skin animal model showed that it decreases the inflammatory disease in this model.

As with any successful anticancer drug, the present invention should kill or incapacitate cancer cells without causing excessive damage to normal cells. This ideal situation is achievable by inducing apoptosis in cancer cells. The JEM-12-25 plant extract exhibited potent inhibition or killing of tumor cells in vitro and in vivo in five different tumor cell lines without adverse side effects. The in vivo results did not demonstrate any toxicity even at high dosages. It is believed that the anti-cancerous effect is a result of cytotoxicity of the extract, similar to chemotherapy and radiotherapy but lacking the side effects. Both extracts also have an immune stimulating effect which may play a role, and it is expected that further testing will quantify this.

3. Identification of the Bioactive Molecule

Liquid chromatography with in-line mass spectrometer (LC-MS) was conducted on the JEM-12-25 to determined the bioactive molecule under the following parameters:

Mobile Phase A: 10 mM Ammonium Acetate in 75% HPLC grade water/25% Acetonitrile

Mobile Phase B: 100% Acetonitrile

Chromatography Mode Reverse phase

Injection volume: 5 μl

UV detection: Absorbance at 210 nm, 254 nm, 280 nm

Mass analysis: ToF with ESI

High Performance Liquid Chromatography (HPLC) Gradient as follows . . .

| Time | Solvent B % | Flow Rate (mL/min) |
|---|---|---|
| 0.0 | 0 | 0.2 |
| 2 | 0 | 0.2 |
| 32 | 60 | 0.2 |
| 34 | 100 | 0.2 |
| 38 | 100 | 0.2 |
| 39 | 0 | 0.2 |

Total ion chromatograms were analyzed by the software package Analyst™ in order to obtain the respective mass spectra across the specified time ranges.

More specifically, high resolution Liquid Chromatography/Mass Spectrometry/Mass Spectrometry (LC-MS/MS) analyses were conducted on JEM-12-25 by electrospray ionization with time of flight in both positive and negative modes which detected a series of masses in these samples ranging from 133 m/z to 134 m/z.

Figure 21:
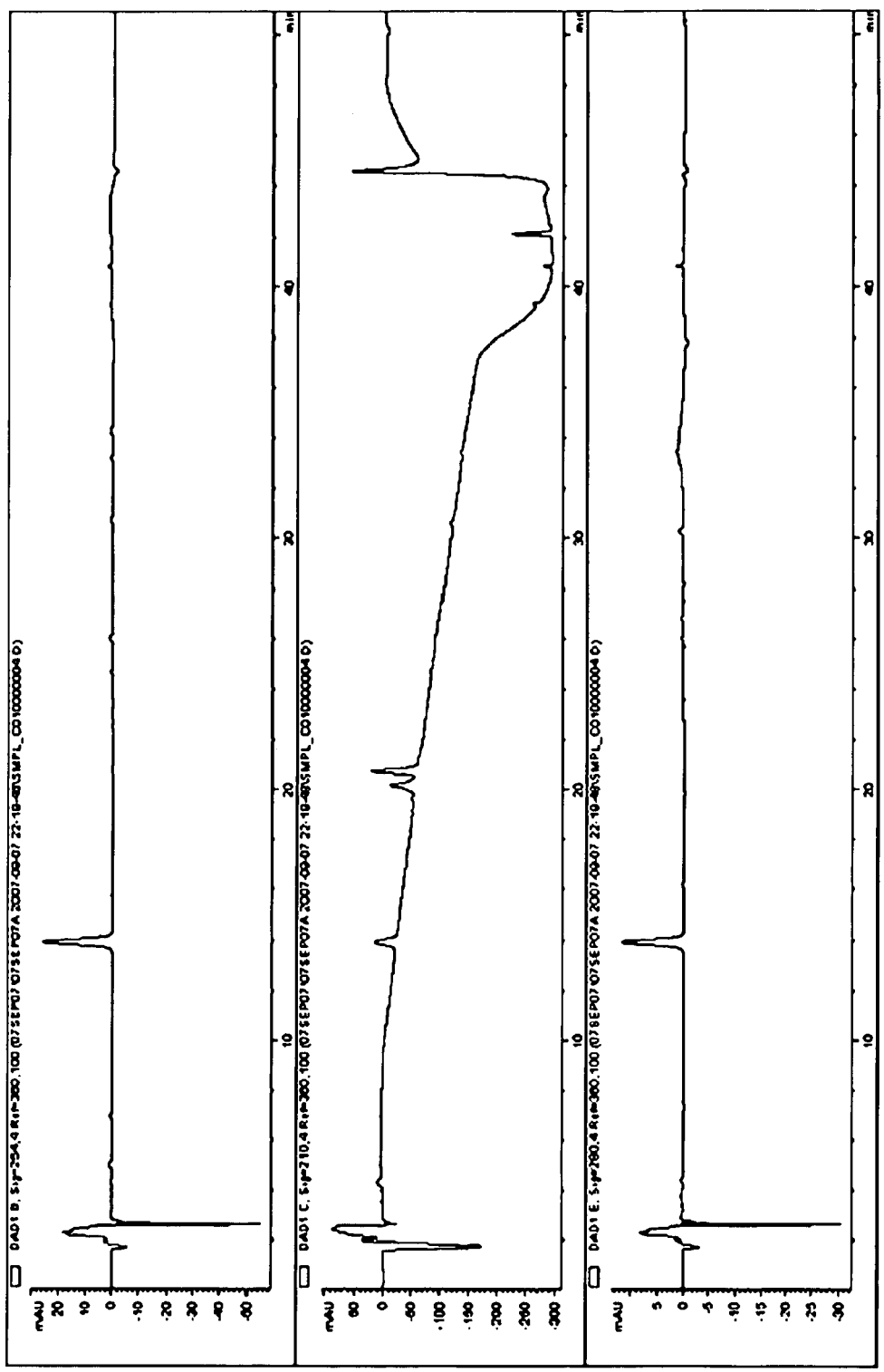
FIG. 21 is a chromatograms of JEM-12-25

FIG. 21 is a chromatograms of JEM-12-25 (top panel—254 nm detection wavelength, middle panel—210 nm detection wavelength, bottom panel—280 nm detection wavelength). Sample JEM-12-25 showed only three significant peaks at 210 nm; of these, the peak at 14 minutes was also detectable at 254 nm and 280 nm, and the doublet at ca. 20 minutes that did not absorb at either 254 nm or 280 nm. The analysis indicates that JEM-12-25 had a doublet eluting between 21 and 22 minutes at 210 nm that yielded strong signals at 809.5 and 821.5 m/z in positive mode and 808.0 m/z in the negative mode. No obvious mass signal was detected for the peak at 14 minutes (210 nm, 254 nm, 280 nm). These results confirm that JEM-12-25 contain the fewest numbers of components. The doublet seen between 20 and 22 minutes for JEM-12-25 contained species with m/z values of 808.0 in negative ionization mode and 809.5 and 821.5 in positive ionization mode. No ionizable species were detected for the peak eluting at 14 minutes. The average molecular weight of the doublet in JEM-12-25 was 808.0216.

Since JEM 12-25 also had the highest anticancer bioactivity (lowest EC50) and the 808-809 mass doublet was unique to JEM-12-25, further fragmentation analyses were conducted on this compound (peak) by LC-MS-MS and LC-MS-MS-MS. For this an Agilent HPLC 1100 mass spectrometer was used along with an Ion trap-MS 6340. Sample was diluted 1:2 in mobile phase and was introduced into the mass spectrometer by infusion via syringe pump at a rate of 0.25 uL/min. Detection was by IT-MS-MS in positive and negative ionization modes, with additional fragmentation modes (MS3 and MS4, ETD) applied to yield maximum fragmentation results. The ion trap survey mass spectrum was extracted and deconvoluted to yield the masses provided in Table 1.

TABLE 1

Masses detected by Ion Trap Mass Spectroscopy (MS)

| Ionization mode | Detected mass | Charge state | Molecular mass | Notes |
| --- | --- | --- | --- | --- |
| Negative | 1616.0 | 1− | 1617.0 | oxidized molecule |
| Negative | 1600.1 | 1− | 1601.1 | native molecule |
| Negative | 808.2 | 2− | 1616.2 | oxidized molecule |
| Negative | 800.7 | 2− | 1601.4 | native molecule |
| Positive | 1618.0 | 1+ | 1617.0 | oxidized molecule |
| Positive | 1635.1 | 1+ | 1634.1 | oxidized molecule + amine |
| Positive | 809.7 | 2+ | 1617.4 | oxidized molecule |
| Positive | 818.0 | 2+ | 1635.0 | oxidized molecule + amine |

Fragmentation of the major peaks by both CID and ETD was performed. Table 2 lists representative fragmentation results obtained in negative ion mode. Fragments generated from both the single and doubly-charged precursors yielded similar fragment spectra, indicating that both precursors were identical. In addition, fragmentation of oxidized precursors also yielded oxidized fragments. Fragmentation was performed in positive ion mode, but no unique ions were detected. Based on the fragmentation spectra obtained, the analyte appears to contain at least one (perhaps two) sialic acid moiety. This conclusion is based on the characteristic mass difference of 292 daltons found between the fragment masses at 796.5 and 1088.8. Other fragment masses are less facile to match with known structures, but the mass differences may be consistent with a polysaccharide structure. HPLC and mass spectroscopy results appear to exclude the presence of any aromatic structures.

TABLE 2

Negative ion mode fragmentation (MS-MS)

| Parent/precursor mass Fragment masses | 808.2 mass/charge | 1616.0 mass/charge |
| --- | --- | --- |
| | 385.5 | 692.5 |
| | 386.4 | 720.6 |
| | 409.5 | 721.5 |

TABLE 2-continued

Negative ion mode fragmentation (MS-MS)

| Parent/precursor mass Fragment masses | 808.2 mass/charge | 1616.0 mass/charge |
| --- | --- | --- |
| | 701.6 | 765.3 |
| | 737.2 | 795.6 |
| | 744.1 | *796.6* |
| | 770.1 | *1088.7* |
| | 772.5 | 1089.8 |
| | 786.2 | 1090.7 |
| | 795.6 | 1272.8 |
| | *796.5* | 1273.8 |
| | 819.7 | 1287.3 |
| | *1088.8* | 1296.5 |
| | 1089.8 | 1372.3 |
| | 1229.8 | 1373.2 |
| | 1230.8 | 1374.1 |
| | 1231.8 | 1382.3 |
| | 1400.2 | 1400.1 |
| | 1401 | 1401 |
| | | 1402 |
| | | 1403 |
| | | 1414.1 |
| | | 1415 |
| | | 1475 |
| | | 1476 |
| | | 1477.1 |
| | | 1489.1 |
| | | 1541.2 |
| | | 1542.2 |
| | | 1543.1 |
| | | 1597.9 |
| | | 1599.3 |

Based on the Mass spectral (MS-MS and MS-MS-MS) data, the main species found in sample JEM 12-25 displays a molecular mass of 1601.1 in negative ion mode. The major peak detected at m/z 1617.0 represents the oxidized form of the molecule. Major peaks at m/z 800.7 and 808.2 are the main species and its oxidized form in multiply-charged form. Positive ion mode analysis yielded similar results, although the molecule was detected with several adducts present (see Table 1). It can be concluded that the molecule is a glycoside with a molecular mass of 1601.1 Da (negative mode), containing up to two sialic acids, as based on the double charge state of the molecule at neutral pH conditions. In addition, since the molecule has also been found to carry two positive charges, it is concluded that there must two amines present within its structure. As yet, data base searches did not reveal any known molecules or dimers with these characteristics.

Based on gradient and isocratic HPLC analyses with detection by UV-PDA and ELSD, JEM-12-25 has a UV spectra maxima at 193.7 nm and is a weak absorber suggesting the absence of aromatic groups. No known existing molecules with this spectra and molecular weights were identified. A proton spectrum of JEM-12-25 was acquired and the complexity of the spectrum is indicates the presence of a compound of proposed molecular weight of ~800. Two-dimensional (2D) 750 MHz proton-proton TOCSY (Total Correlation Spectroscopy) was determined at 25° C. to determine correlations for protons in the spin systems (e.g., sugar rings or chains of coupled aliphatic protons). Based on this the molecule of interest appears to be a highly aliphatic compound consisting most likely of 1-3 sugar rings, and probably several aliphatic rings, and possibly a hydrocarbon chain(s). There are at least 6 methyl ($CH_3$) groups, and on the order of 10 $CH_2$ and CH groups. There is also evidence of at least one likely amide to aliphatic proton correlation, lending credence to the MS-based hypothesis that a sialic acid moiety may be present in the molecule. Under the current sample conditions, exchangeable protons are expected to be weak and difficult to observe.

Next, a Proton NMR of sample JEM-12-25 was assessed for structural characterization. Given 400 micrograms of dry material, the sample was dissolved in 200 micro liters of deuterated methanol (99.9% from Cambridge Isotopes), and delivered into a 3 mm NMR tube for analysis on a Varian 600 MHz NMR system at 25 degrees centigrade.

Figure 22:
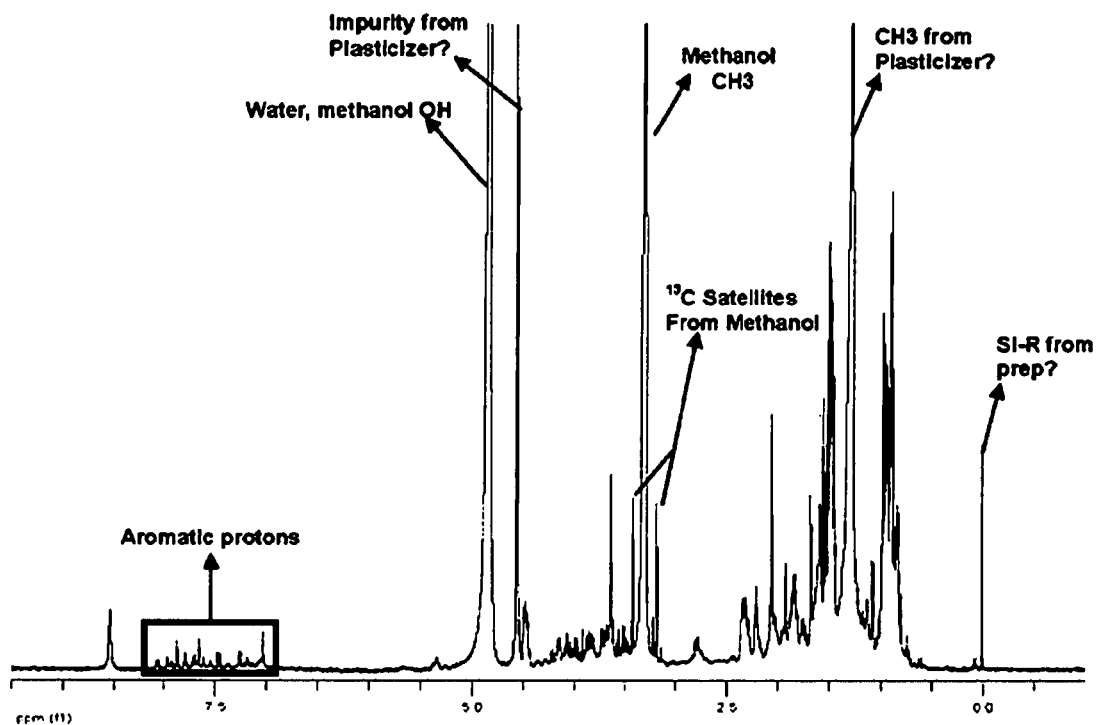
FIG. 22 shows the full spectrum with major peak annotations.

FIG. 22 shows the full spectrum with major peak annotations. The spectrum contains several impurities.

Figure 23:
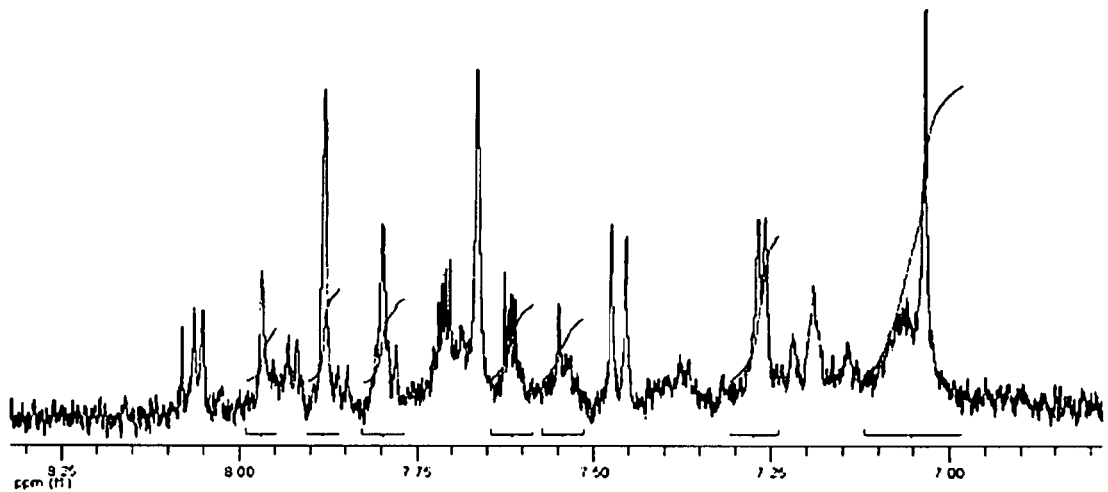
FIG. 23 an expansion of the aromatic region of the spectrum with integrals for a selected number of protons, and is

FIG. 23 an expansion of the aromatic region of the spectrum with integrals for a selected number of protons, and is provided as graphical evidence to support the theory that the sample contains a mixture of compounds. The proton at 7.97 ppm. is assumed to be 1 proton, and all other integrals are relative to this peak. The sample appears to be a mixture of 2 or more compounds.

Finally, an analysis of fraction JEM-12-25 in deuterated methanol based on two-dimensional (2D) 750 MHz proton-proton TOCSY at 25 degrees was conducted. A TOCSY (Total Correlation Spectroscopy) experiment shows correlations for protons in a given spin system. In theory, TOCSY gives connectivity's throughout an entire spin system. Examples of spin systems would be a sugar ring or a chain of coupled aliphatic protons. As such, it is a very useful experiment for characterizing natural products.

Figure 24:
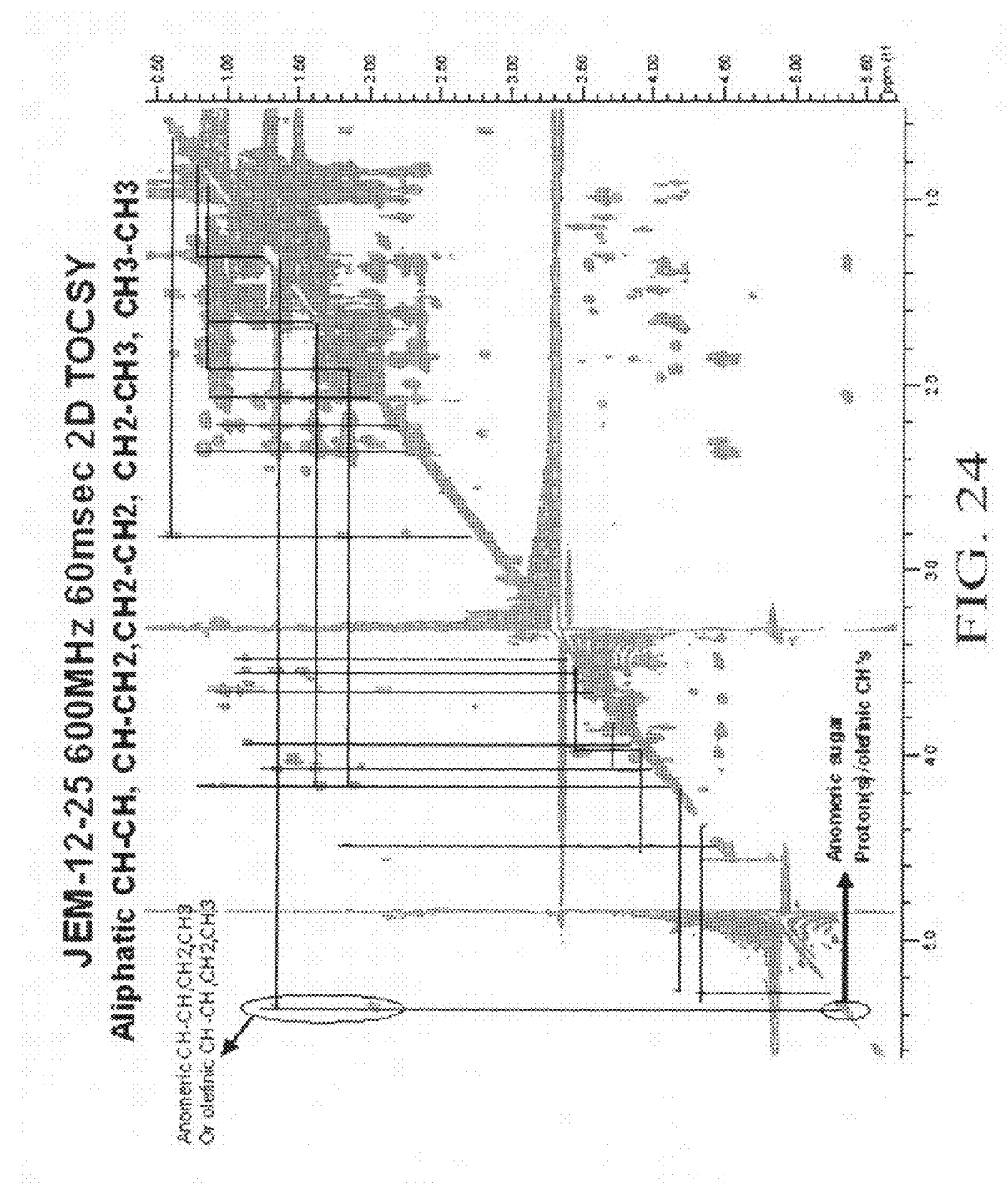
FIG. 24 illustrates the aliphatic Region of the 750 MHz TOCSY Spectrum of JEM-12-25 at 25° C.

FIG. 24 illustrates the aliphatic Region of the 750 MHz TOCSY Spectrum of JEM-12-25 at 25° C. Considering the overall spectrum, it is clear that this sample contains a highly aliphatic molecule such as a carbohydrate. The spectrum contains sufficient detail so as to make the structure determination feasible, though not trivial. The black vertical lines delineate correlations between protons from various functional groups (i.e. CH—CH, CH—CH2, CH—CH3, CH3-CH3) within a given spin system (ring or chain). The horizontal lines indicate connectivity's between protons from different functional groups. It is evident from this spectrum that there are at least a couple of sugar rings, and a relatively large number of CH2 and CH3 groups which form coupled networks of protons. The blue ovals identify peaks that are highly suggestive of the presence of at least one, and probably more, anomeric proton(s) from a sugar ring(s). Due to the relatively complex nature of the spectrum, it is very difficult to obtain definitive numbers of CH2 and CH3 groups, but there are certainly enough to suggest a molecular weight of 800-900 (or even 1600 if it is some sort of dimer).

While FIG. 2 is somewhat speculative at this point, the TOCSY spectrum of fraction JEM-12-25 is indicative of the type of molecule shown. The molecule of interest appears to be a highly aliphatic compound consisting most likely of 1-3 sugar rings, and probably several aliphatic rings, and possibly a hydrocarbon chain(s). There are at least 6 methyl (CH3) groups, and on the order of 10 CH2 and CH groups. There is evidence of at least one likely amide to aliphatic proton correlation, lending credence to the MS-based hypothesis that a sialic acid moiety may be present in the molecule. Under the current sample conditions, exchangeable protons are expected to be weak and difficult to observe.

One skilled in the art should understand that further studies should be conducted including in vitro ADME/TOX (adsorption, distribution, metabolism, elimination and toxicity) studies; cancer cell line selectivity in vitro studies; in vivo animal efficacy and toxicity studies; in vivo pharmacokinetic studies; both in vitro and in vivo mechanism of action (MOA) studies; structure-activity relationship (SAR) studies; and medicinal chemistry studies, all of which should further improve efficacy and reduce toxicity of the JEM-12-25 to improve the therapeutic index.

One skilled in the art should also understand that further studies should produce a method of synthesizing the anticancer bioactive compound JEM-12-25 (versus biomass isolation of the product) using good manufacturing practices, as well as the synthesized JEM-12-25. This method generally comprises the steps of: 1) extracting the *Tillandsia recurvata* plant in an aliphatic alcohol by dissolving the *Tillandsia recurvata* in the alcohol thereby obtaining a suspension, stirring the suspension, filtering the suspension by fritted glass thereby obtaining a first filtrate and a solid part; and 2) extracting the solid part in aliphatic alcohol thereby obtaining a second filtrate and solid part; 3) combining the first and said second filtrate, and 4) air drying the combined filtrate under vacuum thereby obtaining said extract.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. A method of treating cancer comprising the step of administering to a cancerous tumor a composition to induce cancerous tumor cell death by apoptosis, said composition comprising an extract of Jamaican Ball Moss (*Tillandsia recurvata*).

2. The method of claim 1 wherein the composition is administered by subcutaneous injection in an amount to deliver a dosage of the extract effective to cause tumor cell death by apoptosis.

3. The method of claim 1 wherein the composition is administered by subcutaneous injection in an amount to deliver a dosage of the extract that is non-toxic.

4. The method of claim 1 wherein the extract is an aliphatic compound consisting of L sugar rings, where L is an integer between 1-3.

5. The method of claim 4 wherein the aliphatic compound has a plurality of aliphatic rings, and at least one hydrocarbon chain.

6. The method of claim 5 wherein the aliphatic compound has at least 6 methyl (CH3) groups.

7. The method of claim 6 wherein the aliphatic compound has at least 10 CH2 and CH groups.

8. The method of claim 1 wherein the extract comprises a sialic acid moiety.

9. A method of treating cancer comprising:
   extracting from Jamaican Ball Moss (*Tillandsia recurvata*) an aliphatic compound consisting of L sugar rings, where L is an integer between 1-3, a plurality of aliphatic rings, and at least one hydrocarbon chain, at least 6 methyl (CH3) groups, and at least 10 CH2 and CH groups; and
   administering an effective amount of the aliphatic compound to a cancerous tumor by subcutaneous injection to induce cancerous tumor cell death by apoptosis, while showing no detrimental side effects on normal, non-cancer related cells.

* * * * *